United States Patent [19]

Aubard et al.

[11] Patent Number: 5,266,599

[45] Date of Patent: Nov. 30, 1993

[54] USE OF (+)-1-[(3,4,5-TRIMETHOXY)-BENZYLOX-YMETHYL]-1-PHENYL-N,N-DIMETHYL-N-PROPYLAMINE TO INCREASE GASTRIC DISCHARGE IN A SUBJECT

[75] Inventors: Gilbert G. Aubard, Palaiseau; Alain P. Calvet, L'Hay-les-Roses; Agnès Grouhel, Meudon; Henri Jacobelli, Paray-Vieille Poste; Jean-Louis Junien, Sevres; Xavier B. Pascaud, Paris; François J. Roman, Courbevoie, all of France

[73] Assignee: Jouveinal S.A., Paris, France

[21] Appl. No.: 931,994

[22] Filed: Aug. 19, 1992

Related U.S. Application Data

[63] Continuation of Ser. No. 367,603, Jun. 19, 1989, abandoned.

[30] Foreign Application Priority Data

Feb. 20, 1989 [FR] France ................. 89 02177

[51] Int. Cl.[5] .......................................... A61K 31/135
[52] U.S. Cl. .................................. 514/651; 514/928; 564/304; 564/346
[58] Field of Search ................ 564/304, 346; 514/651, 514/928

[56] References Cited

U.S. PATENT DOCUMENTS

| 3,649,691 | 3/1972 | Shavel et al. | 564/304 X |
| 3,814,750 | 6/1974 | Cross et al. | 564/346 X |
| 4,301,163 | 11/1981 | Torossian et al. | 564/346 X |
| 4,588,746 | 5/1986 | Watthey | 564/304 X |

OTHER PUBLICATIONS

Burger, "Medicinal Chemistry", 3rd Ed., pp. 81–83 (1970).

Primary Examiner—Richard L. Raymond
Attorney, Agent, or Firm—Pennie & Edmonds

[57] ABSTRACT (+)-1-[(3,4,5-trimethoxy)-benzyloxymethyl]-1-phenyl-N,N-dimethyl-n-propylamine of formula

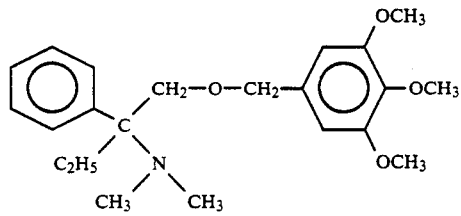

is a medicament of use in gastroenterology.

27 Claims, No Drawings

USE OF (+)-1-[(3,4,5-TRIMETHOXY)-BENZYLOXYMETHYL]-1-PHENYL-N,N-DIMETHYL-N-PROPYLAMINE TO INCREASE GASTRIC DISCHARGE IN A SUBJECT

This is a continuation of application Ser. No. 07/367,603, filed Jun. 19, 1989, now abandoned.

The object of the present invention is a medicament which, when administered orally, increases the gastric discharge, on the one hand, and, on the other, is antispasmodic thus having an influence on various disorders of the gastrointestinal tract.

It is known that gastric discharge may be increased or accelerated by various compounds. So, metoclopramide which since 1964 has been suggested as an antiemetic and modifier of digestive behavior possesses this property. However, this product which belongs to the group of neuroleptic drugs requires delicate use, as indicated by the contra-indications, precautions for use, medicinal interactions and undesired effects cited in the "Dictionnaire Vidal"- Ed. 1988 p. 1320.

Therefore, the restrictions indicated for its use in combination with anticholinergic derivatives, antiparkinsonian compounds and neuroleptic drugs, with which activity inhibitions as well as possible centrally acting synergies are reported, limit in particular its indication.

M. Gué et al. (Gastroenterol. Clin. and Biol., 1988, 12, 2) have recently shown that two compounds hitherto known for their analgesic property cause an increased gastric discharge in the dog, when administered orally. The authors explain this phenomenon by the fact that these products, i.e. Tifluadom and U-50.488, have a special affinity for the opiate receptors of the kappa type and probably act locally on these receptors situated in the gastric mucous membrane to bring about an increased discharge.

However, these compounds are mainly known to have a general analgesic activity, of opiate type, when administered orally (Pharmaprojects - V & D Publications, Ltd - May and August 1988).

Reportedly, this activity does not bring about a dependence effect, like morphine, but is accompanied by a tolerance phenomenon which requires the product to be administered in increasing quantities in order to achieve the desired effect.

So far these compounds have only been used as pharmacological reagents and are not known to have been used in human therapy in the form of drugs.

The present invention has as its object a medicament acting on the gastrointestinal tract by both an antispasmodic effect and by the effect of increasing gastric discharge, these actions, however, having more or less no central effect and dependence or addiction phenomena.

The medicament is characterized in that it contains as active ingredient the dextrorotatory enantiomer of an ether amino oxide: (+) 1-[(3,4,5-trimethoxy)benzyloxymethyl]-1-phenyl-N,N-dimethyl-n-propylamine of formula

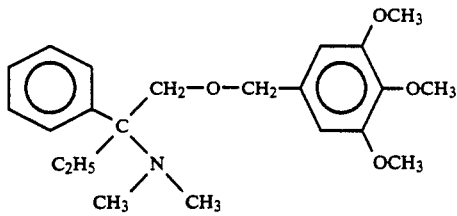

and its pharmaceutically acceptable acid addition salts.

The present invention was realized in an unforeseen manner by successive studies, the essential feature of which is described as follows:

In U.S. Pat. No. 4,301,163 the applicant has claimed protection for aminoethers having local anaesthetic, spasmolytic and analgesic properties.

In order to define more precisely this last property of the compound mentioned in Example 2 of the patent, the optical resolution of this racemic product was carried out to produce, on the one hand, the dextrorotatory enantiomer which is the product of this invention and, on the other hand, the levorotatory enantiomer.

It is recognized that the "in vitro" study of the opiate receptor binding affinity is a means of studying potentially analgesic compounds (Opiate receptor binding in Drug Research. Eric J. Simon in "Receptor binding in Drug Research" p. 183–202 - Ed. Robert A. O'Brien-Dekker-1986).

The optically active compounds as well as those preferred in the U.S. Patent, the product called U 50.488 and morphine as reference product were involved in this test according to the method described by F. Roman et al. in J. Pharm. Pharmacol. 1987, 39, p. 404–407.

At the end of the study it was found that the product of the invention distinguishes itself from the other compounds by the fact that it shows a receptor binding affinity to the receptors mu, delta and kappa studied which is in contrast to the preferred compounds of the aforementioned U.S. Patent, which show above all a mu affinity, and to the compound U 50.488 which, as reported, binds specifically to the kappa receptors. These results are indicative of the potential analgesic activities of these products (CRC Handbook of Stereoisomers: Drugs in Psychopharmacology CRC Press, Inc - 1984 p. 402); they were thus involved in an "in vivo" test considered to be suitable for determining this effect.

Surprisingly, the compound of the invention was virtually without any analgesic effect in this test, in contrast to other products which show themselves to be active.

A last attempt to determine the expression "in vivo" of the properties found "in vitro" in relation to the product has now been made using the test carried out by M. Gué et al. (Reference already cited).

When tested, the product of the invention clearly shows an activity which encourages gastric discharge of solids in dogs. Moreover, the effect observed is inhibited by compounds recognised to be opiate antagonistic.

Hence, in an unexpected and special manner, the compound of the invention which shows an "in vitro" affinity with the opiate receptors mu, delta and kappa does not have "in vivo", as one would expect it, a central analgesic activity, but a local activity on the opiate receptors of the gastric mucous membrane, thus bringing about increased discharge of solids in dogs.

Moreover, it is also remarkable that the product possesses an antispasmodic activity as well.

Hence, in an aqueous solution, and at a $1.70 \times 10^{-5}$ molar concentration the product inhibits 50% of the amplitude of spasms caused by barium chloride on the duodenum of the rat. In this test which is carried out "in vitro", morphine is inactive at a concentration of more than 5 times greater than that of the product of the invention.

The double effect of the product demonstrated by the increased gastric discharge of the solids and the disappearance of intestinal spasms is particularly significant on account of the extent of the actions on the various stages of the gastrointestinal tract.

Numerous disorders of the tract may well be treatable. Among other examples, mention is made of gastrointestinal disorders caused by treatment with medicaments over a long period, such as certain analgesic or neuroleptic medicaments.

Thus, the product of the invention is suitable for normalizing the activity of the gastrointestinal tract in patients treated with analgesic compounds of the morphine type which are known to slow down gastric discharge and cause spasms of certain intestinal muscles (Goodman and Gilman's "The Pharmacological Basis of Therapeutics" - 6th ed. 1980 - p. 503 to 504).

The tests and results mentioned above and which are the basis of the invention are described in more detail in the following.

The comparative tests which made it possible to determine the particular properties of the products of the invention, more particularly of (+) 1-[(3,4,5-trimethoxy)-benzyloxymethyl]-1-phenyl-N-N-dimethyl-n-propylamine D-(−)-tartrate, which is preferred, have been carried out with racemic compounds of U.S. Pat. No. 4,301,163, namely (+/−)1-[(3,4-dimethoxy)benzyloxymethyl]-1-phenyl-N,N-dimethyl-n-propylamine, (+/−)1-benzyloxymethyl-1-phenyl-N,N-dimethyl-n-propylamine, (+/−) 1-[3,4,5-trimethoxy)benzyloxymethyl]-1-phenyl-N-methyl-n-propylamine and (+/−) 1-(p-chlorobenzyloxymethyl)-1-(p-methoxyphenyl)N,N-dimethyl-n-ethylamine which are respectively the products of Examples 1, 3, 12 and 13 described and declared to be the preferred ones of this patent.

Moreover, also used as products of comparison were:

the levorotatary enantiomer of the compound of the invention, i.e. (−) 1-[(3,4,5-trimethoxy)benzyloxymethyl]-1-phenyl-N,N-dimethyl-n-propylamine, the preparation of which is described in the experimental part of the text, trimebutine (DCI) which is (+/−)-2-dimethylamino-2-phenyl-n-butyl 3,4,5-trimethoxybenzoate, the object of French Patent No. 2 369 M and which has a chemical structure similar to that of the racemic compound which corresponds to the product of the invention.

The compound coded U 50.488 described above as being active in gastric discharge, i.e. trans-3,4-dichloro-N-methyl-N-[2-(1-pyrrolidinyl)-cyclohexyl]-phenylacetamide which is recognized to be a centrally acting analgesic and antiepileptic (Pharmaprojects - published August 1988).

Finally, in these tests morphine has been used as an analgesic reference substance.

The activity of the enantiomer has, therefore, been compared to that of racemic compounds. However, it is known that in practical tests the receptors involved are stereo-selective and that they are only susceptible to the activity of one single enantiomer, the other being inactive, as has been described in the "CRC Handbook of Stereoisomers" Ed. Donald F. Smith. 1984, p. 401 to 440: "Opiates agonists and antagonists: Pharmacological behavorial, and neurochemical effects of stereoisomers". In the tests carried out and with regard to the comparisons this fact has been taken account of, and for a racemic compound the number of the result of the test will be multiplied by two and for a result of given value the dose of the racemic product responsible for the effect will be divided by two, before comparing it with the result of the compound of the invention.

As has already been mentioned, the binding affinity of the products to the opiate receptors mu, delta and kappa was measured according to the method described by F. Roman et al. (cited above).

The results are shown in the following Table 1 and are expressed in $CI_{50}$ representing the nanomolar concentrations of the dissolved product capable of inhibiting 50% of the binding of a specific radioactive ligand to the receptor studied.

TABLE 1

| Binding affinity of the compound and of the products of comparison to the receptors mu, delta and kappa | | | |
|---|---|---|---|
| Test compound | mu receptor | delta receptor | kappa receptor |
| Product of the invention | | | |
| (+) Enantiomer | 196 | 540 | 232 |
| (−) Enantiomer | 580 | 12 320 | 2 630 |
| Ex. 1 of U.S. Pat. No. 4,301,163 | 1 110 | 7 800 | 1 110 |
| Ex. 3 of U.S. Pat. No. 4,301,163 | 190 | 14 700 | 560 |
| Ex. 12 of U.S. Pat. No. 4,301,163 | 360 | 2 250 | 2 280 |
| Ex. 13 of U.S. Pat. No. 4,301,163 | 250 | 4 390 | 900 |
| Trimebutine | 146 | 1 750 | 1 460 |
| U. 50.488 | 1 028 | 14 610 | 66 |
| Morphine | 7 | 152 | 127 |

When considering these results and even when making the correction suggested above to the racemic compounds, which has not been mentioned in Table 1, it is remarkable that the dextrorotatory enantiomer of the invention is the only compound with morphine showing an affinity to the three receptors studied, with a non-negligible intensity.

On the other hand, when looking only at the mu receptor, the compounds of the Examples 3, 12 and 13 of the U.S. Patent as well as trimebutine are just as, if not more active. The same applies to the compound U. 50.488 if one considers only the kappa receptor.

As the compound affinity to opiate receptors (in vitro) is often representative of analgesic pharmacological properties (CRC Handbook of Stereoisomers - cited above), the products were involved in a test "in vivo" suitable to demonstrate this analgesic activity in general.

This test carried out on mice according to a method derived from that of Koster R. (Fed. Proc. 1959, 18, p.412) consists in studying the influence of products administered orally to the animal, on the manifestations of pain, caused by administering an acetic acid solution intraperitoneally.

For this purpose, the animals in groups of 10 are given nothing to eat or to drink for 20 hours before the test. However, they receive the products to be studied as an aqueous solution at the rate of 2 ml of solution per 100 g body weight, then 10 minutes later an intraperitoneal injection of 0.25 ml of an acetic acid solution at 0.5% (v/v) kept at 37° C. Three minutes after this injection the number of abdominal cramps shown by the animals are counted for 10 minutes. The animals are considered to suffer less pain, if they show a number of cramps which is below half the average of the cramps shown by animals of the control group. In the test the products have been administered in a dose of 50 mg per kg, morphine used as reference and administered orally at a rate of 10 mg per kg showing an analgesic effect of 78%.

Table 2 shows the results of this study. They demonstrate and confirm the characteristics of the product of the invention which shows very little analgesic effect compared to the other compounds studied. These findings are all the more marked, if the suggested correction has been applied for these racemic compounds. In this case, the dextrorotatory enantiomer of the invention (17.60%) is virtually 3 times less analgesic than the trimebutine (24.3×2=48.6%) and 5 times less (44.0×2=88.0%) than the compound of Example 12 of the U.S. Patent.

TABLE 2

| Analgesic activity "in vivo" (50 mg/kg - orally) | |
|---|---|
| Test Compound | % analgesia (p) |
| Product of the invention | |
| (+) Enantiomer | 17.6 (*) |
| Ex. 3 of U.S. Pat. No. 4,301,163 | 27.6 (*) |
| Ex. 12 of U.S. Pat. No. 4,301,163 | 44.0 (***) |
| Ex. 13 of U.S. Pat. No. 4,301,163 | 27.9 (***) |
| Trimebutine | 24.3 (**) |
| U. 50.488 | 90.0 (***) |

(p) probability - Student's T test
(*) p < 0.05
(**) p < 0.01
(***) p < 0.001

The research on the local activity of the product of the invention on the opiate receptors of the gastric mucous membrane has been carried out according to a method following that described by M. Gué et al. (already mentioned).

The authors study the action of opiate compounds of type mu and type kappa in dogs after oral administration. When weak doses are used, they do not observe an effect for the mu agonist compounds, whereas the kappa agonist type of compounds (such as U. 50.488) further the gastric discharge of the solid phase of the meal in dogs. This effect had, by the way, been inhibited by the opiate antagonistic compounds naloxone and MR 2266 which are known to be antagonistic to both the mu and kappa receptors (D. Römer et al., Life Sciences, 31, p. 1217-1220, 1982).

In this study, the authors put forward the proposition that the opiate compounds of the kappa agonist type, such as trifluadom and U. 50.488, when administered orally, modify the gastric discharge by their local action.

In an attempt to show such an action with the product of the invention, this has been used in this test, compared with its levorotary enantiomer and trimebutine which is known for its regulatory activity of the gastrointestinal functioning.

The principle of the test consists in measuring the gastric content of the animals one hour after eating a meal comprising 400 g of solid matter with 21.7% dry matter composed of:
7.7% proteins,
4.5% lipids,
6.9% carbohydrates
2.6% mineral salts and 20 g of sheeps liver containing radiolabelled cyanocobalamine. The meal is consumed within about 5 minutes by the animals. After one hour, the gastric content is collected by means of a small tube placed approximately 10 cm into the pyloris before the experiment.

The collected sample is weighed and homogenized. Its radioactivity is measured and the amount of the gastric discharge expressed in percentage is calculated according to the formula:

$$\% \text{ discharge} = \frac{(cpm1 \cdot P1 - cpm2 \cdot p) \times 100}{cpm1 \cdot P1}$$

in which:

cpm1 represents the radioactivity per gram of the mixed, radiolabelled liver,

P1 is the weight of the radiolabelled liver, added to the meal, cpm2 is the radioactivity per gram of collected sample after one hour, p is the weight of this sample collected after one hour.

In practice, each test is carried out on three dogs and consists in administering to them, 20 minutes before eating the meal described above, a capsule containing the test product at a dose of 0.25 ml per kg animal weight or a capsule placebo which serves to determine the control phenomenon of the discharge on the animal. The 3 dogs receive each treatment twice in random order. Finally, in a last series of tests 3 dogs receive an intravenous administration of a solution of MR 2266 or naloxone at the rate of 0.1 mg per kg of weight. The meal is presented and ingested 20 minutes after the capsule containing the test product has been administered. The evacuation values of the solid phases are measured as described before and compared using the test of Mann and Whitney (U test). The difference in comparison with the control values is considered significant when p is < or = 0.05.

The effect of the test products is objectivised by the percentage variation calculated according to the relation:

$$\% \text{ variation} = \frac{(\% \text{ test evacuation} - \% \text{ control evacuation}) \times 100}{\% \text{ control evacuation}}$$

The results obtained for this study are shown in Table 3.

TABLE 3

| Effect of the products on the gastric evacuation of solids in dogs | |
|---|---|
| Test product (*) | Variation in % |
| Product of the invention | |
| (+) Enantiomer | +110% |
| id. + naloxone | +5% |
| id. + MR 2266 | +14% |
| enantiomer (-) | +26% |
| Trimebutine | -4% |

(*) With the exception of the trimebutine which was administered in a dose of 5 mg/kg, the products were administered at the rate of 0.25 mg/kg according to the protocol described above.

The action of the product of the invention is undeniable: its effect doubles the gastric evacuation of the solids in dogs one hour after administration, whereas the effect of its levorotatory enantiomer is four times less significant. Moreover, the action observed is inhibited at the same time by naloxone, which is more particularly antagonistic to the mu receptors, and MR 2266 which is antagonistic to the kappa receptors, which makes it possible to attribute the discharge effect to a general activity of the agonist type on the local opiate receptors of the gastric mucous and more particularly on the mu and kappa receptors.

The antispasmodic activity of the product of the invention in the form of its D (−)-tartrate has been researched "in vitro" on the duodenum of the rat which is an essential part of the intestinal tract of this animal.

The study consists in bringing about, on a fragment of this tissue, contractions caused by a spasmogen agent which is barium chloride in this study, and then in calculating the concentration ($IC_{50}$) of the solution of the product capable of inhibiting 50% of the amplitude of the contractions caused.

The results of the study are shown in Table 4

| Antispasmodic activity "in vitro" on the duodenum of rats (Spasmogen $BaCl_2$) | |
|---|---|
| Test product | $IC_{50}$ mol. liter |
| Product of the invention | |
| (+) Enantiomer | $1.70 \cdot 10^{-5}$ |
| Papaverine | $2.74 \cdot 10^{-5}$ |
| Morphine | Inactive at $10^{-4}$ |

Although morphine is inactive in this test, the product of the invention shows an activity slightly above that of papaverine which is considered to be the reference compound for th spasmolytic activity.

Finally, the study of the acute toxicity of the product of the invention is also significant in particular with regard to its levorotatory enantiomer.

This toxicity has been studied orally in male mice. The test products have been administered at the rate of 2 ml of their aqueous solution per 100 g of animal weight. The animals are then observed for 3 hours after administration, then daily for fourteen days, when they are sacrificed and then an autopsy is carried out.

The $LD_{50}$ (lethal doses which cause the death of 50% of the animals) have been calculated according to the method of Reed J. L. and Muench H. (Am. J. Hyg. 1939, 27, p. 493). The results obtained are shown in the following Table 5 and show that the product of the invention is about half as toxic in this test than its levorotatory antipode.

TABLE 5

| High toxicity, by oral method, in mice | |
|---|---|
| Test product | $LD_{50}$ mg/kg |
| Product of the invention | |
| (+) Enantiomer | 407 |
| (−) enantiomer | 255 |

The studies described above undoubtedly show the significance of the product of the invention, the particular properties of which consisting, on the one hand, in a local activity of agonist type on the opiate receptors on the gastric mucous and, on the other hand, in an antispasmodic activity, in particular at the intestinal level, justify its dual usefulness in treating digestive disorders, to which gastric motility is linked, such as the gastro-oesophagian reflux, ulcers, dyspepsia, gastritis, functional colopathy and biliary dyskinesia.

As active ingredient of the medicament according to the invention the free amine may be used which is (+)-1[(3,4,5-trimethoxy)-benzyloxymethyl]-1-phenyl-N,N-dimethyl-n-propylamine, or its addition salts with the pharmaceutically acceptable organic or mineral acids. As such hydrochloric, hydrobromic, phosphoric, sulphuric acids as well as acetic, citric, gluconic, maleic acids are used. As far as the organic acids are concerned, D-(−) tartaric acid gives the preferred addition salt with the compound of the invention since, on the one hand, its purification by crystallization in ethanol is easy and efficient and, on the other hand, it is soluble in water and, therefore, suitable for the preparation of aqueous pharmaceutical forms without being hygroscopic. It has the physico-chemical stability necessary for its use as an agent in the pharmaceutical industry.

A further aspect of the invention is a process for preparing the dextrorotatory aminoether oxide and its D-(−) tartrate which may be obtained:

by the preferred process similar to that described in U.S. Pat. No. 4,301,163 and which consists in reacting (+)-2-dimethylamino-2-phenyl-n-butanol prepared according to the method described in the Japanese patent application published under No. 16416/1980 on 1st May 1980, with a 3,4,5-trimethoxybenzyl halide of formula

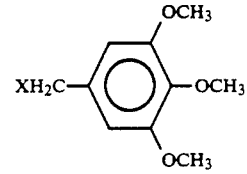

in which X is a halide atom which is chlorine, bromine or iodine.

This means more precisely that, firstly, a metallic alcoholate of the dextrorotatory aminoalcohol is prepared by reaction with an alkali metal, such as sodium, potassium or their hydrides or amides. This reaction is generally carried out in aromatic solvents, such as benzene, toluene, xylene or in ethereal solvents, such as diethyl ether, dioxane, tetrahydrofuran or in solvents such as dimethylsulphoxide, dimethylformamide, acetonitrile, dimethylacetamide, hexamethylphosphoro-triamide. The salification reaction is effected by using 0.7 to 1.5 moles of metallic reagent per mole of alcohol and, preferably, 0.9 to 1.2 moles of said reagent. The salification temperature is between 0° and 140° C., more particularly between 20° and 110° C.

The metallic salt of the amino alcohol is formed after a reaction time of 30 minutes to 6 hours, then it is condensed with the 3,4,5-trimethoxybenzyl halide at a temperature of between 0° and 140° C., preferably 70° to 110° C. The condensation lasts between 1 to 24 hours, preferably between 2 and 6 hours, and may be followed towards the end of the reaction by thin layer chromatography. The separation of the product formed is carried out by conventional methods described in the illustrating Example.

The dextrorotatory amino ether oxide obtained may be salified with the suitable acids already mentioned. In a preferred manner, this operation may be carried out by using D-(−) tartaric acid at the rate of 0.75 to 1.25 mole per mole of the product to be salified. The reaction is carried out in solvents, such as ketones or alcohols of low molecular weight. Ethanol is preferred, used at the rate of 3 to 10 volumes per part by weight of isomer. Hence, for 1 mole, 5 to 7 volumes per weight of ethanol and 0.95 to 1.05 mole of D-(−) tartaric acid are usually added. The reaction is carried out at a temperature of between 20° and 80° C. lasting between 15 minutes to 5 hours, more particularly between 30 minutes and 1 hour at a temperature between 35° and 50° C. The crystallization of the salt is completed after 48 hours at 20° C. after which the D-(−) tartrate of the dextrorotatory isomer of the invention may be obtained by filtration in a state of purity which is satisfactory for its therapeutic use. However, if necessary, the product may be purified by recrystallization in ethanol, i.e. by resolution of the racemic amino ether oxide prepared as in Example 2 of U.S. Pat. No. 4,301,163.

In a conventional manner, this resolution is effected by separating diastereoisomers formed after salification with optically active acids. This process is commonly practiced. A particularly comprehensive compilation of the reagents and their use can be found in "Optical Resolution Procedures for Chemical compounds'-'—Vol. 1: Amines and related compounds. Paul Newman—1978.

In more precise terms the process consists in salifying the corresponding racemic propylamine, dissolved in a solvent which may be a ketone or an alcohol with a boiling point below or near 80° C., by using a (+) dextrorotatory organic acid to yield an insoluble (+)-acid/(−)-propylamine salt; in removing this insoluble salt by filtration in order to obtain a solution containing both (+) acid and the (+) enantiomer of the n-propylamine; in evaporating the solvent of this solution to dryness in order to obtain a residue, in dissolving the residue in water and in alkalising the solution up to a pH near or above 10 by adding an alkali metal or alkaline earth or ammonium hydroxide solution, in extracting the free dextrorotatory n-propylamine with an organic solvent, and then in evaporating the extracted organic solvent in order to obtain the desired (+)-n-propylamine.

When carrying out this method of resolution, tartaric acid enantiomers are preferred. When using these, diastereoisomers are formed in a first phase with L-(+)-tartaric acid, the diastereoisomer formed between the acid and the levorotatory enantiomer which crystallises is then removed by filtration, the filtrate is then treated to free its salt and to separate the dextrorotatory isomer of n-propylamine which is the object of the invention and finally, the addition salt is prepared with D-(−)-tartaric acid, the salt which may finally be purified as described above.

In order to effect the resolution of one mole of racemic compound, 0.6 to 1.5 moles of L-(+)-tartaric acid are used to salify the amine in a solvent which, preferably, is an alcohol or a ketone of low molecular weight and a boiling point near or below 80° C. This solvent should preferably be anhydrous. Absolute ethanol is most frequently used at the rate of 3 to 30 parts by volume per part by weight of compound to be treated.

Salification is carried out by heating the solution obtained for 5 minutes to 1 hour under reflux of the solvent, then by cooling to allow the diastereoisomer formed from L-(+)-tartaric acid and the levorotatory enantiomer of the compound of the invention to crystallise.

This salt which is a by-product is removed by filtration. The filtrate is then treated in a suitable manner in order to obtain the dextrorotatory enantiomer of the invention. To this end, the solvent is removed by distillation, the residue is taken up in an alkaline solution in a sufficient quantity in order to obtain a pH near or above 10, the product of the invention is then extracted in a suitable solvent, such as ether or methylene chloride.

After evaporating this extracted solvent, the dextrorotatory enantiomer of the invention is purified as described above by forming an addition salt, particularly with D-(−)-tartaric acid which is preferred, then purified by crystallising this salt.

These processes are illustrated in a non-restrictive manner in the experimental part by way of examples which describe the process and characteristics of the products of the invention obtained.

The usefulness of the product of the invention and its salts has been shown in the treatment of various disorders of digestive motility. According to the nature and seriousness of the disorder to be treated the daily therapeutic dose should contain between 5 and 1000 mg, preferably between 25 and 500 mg of the product, which may be taken once or several times.

The product is presented in conventional pharmaceutical form, such as tablets, capsules, suppositories, solutions or suspensions which are suitable for drinking, spraying or injecting.

For the galenic or so-called "dry" forms the quantity active ingredient may be 5 to 80% by weight of the finished product, the total of the excipients may be at the rate of 95 to 20% of said weight. In the so-called "aqueous" forms (suspensions and solutions) the active ingredient may be 0.1 to 20% by weight of the composition, water and various additives representing 99.9 to 80% of the total weight of the finished preparation.

The preparations of injectable solutions at 0.5% (w/v) and the preparation of coated tablets of a dose of 100 mg (−)-tartrate of the compound of the invention per unit are shown by way of illustration Formulations

*Injectable solution, 0.5% (w/v)

Compounds for the preparation of 100 ml of solution:

| | |
|---|---|
| (−)-tartrate of (+)-1-[(3,4,5-trimethoxy)benzyloxymethyl]-1-phenyl-N,N-dimethyl-n-propylamine | 0.500 g |
| sodium chloride for injections | 0.850 g |
| distilled water for injectable preparations q.s.p | 100.0 ml |

Preparation

The compounds are dissolved in approximately 95% of the quantity of distilled water prescribed for the preparation, at a temperature around 20° C., while stirring. The solution obtained is filtered through a membrane of a porosity of 22 microns, then the filtrate made up to the exact volume with distilled water which has also been filtered. The solution is packaged at a rate of 5 ml per ampoule, the ampoules are then sealed and sterilised at 121° C. for 30 minutes.

*Coated tablets with 100 mg of agent per unit

Formula per unit

| | |
|---|---|
| (−)-tartrate of (+)-1-[(3,4,5-trimethoxy)benzyloxymethyl]-1-phenyl-N,N-dimethyl-n-propylamine | 100.0 mg |
| dicalcium phosphate | 30.0 mg |
| lactose | 132.0 mg |
| maize starch | 80.0 mg |

-continued

| | |
|---|---|
| carboxymethyl cellulose | 10.0 mg |
| polyvinylpyrrolidone 25 | 16.0 mg |
| microcrystalline cellulose | 20.0 mg |
| magnesium stearate | 4.0 mg |
| talcum | 8.0 mg |
| hydroxypropylmethyl cellulose | 4.4 mg |
| titanium dioxide | 1.1 mg |
| for a total of | 405.5 mg |

Preparation

The following is introduced into a mixer-kneader:

| | |
|---|---|
| active ingredient | 1750 g |
| dicalcium phosphate | 525 g |
| lactose | 2320 g |
| maize starch | 1400 g |
| carboxymethyl cellulose | 175 g | for moistening a solution of 1.05 g of polyvinylpyrrolidone 25 in 770 ml of purified water is added to the mixture obtained. The mixture is granulated in an apparatus fitted with a 2 mm mesh, the grains are oven-dried at 50° C., then calibrated by passing them through a 1 mm mesh.

346 g of microcrystalline cellulose, 69 g of magnesium stearate and 139 g of talcum are added to 6365 g of these granules in a mixer. After mixing, the product is compressed to 401.5 mg per unit, the tablets obtained are coated in a centrifuge at 40° C. using an aqueous suspension of titanium dioxide and hydroxypropylmethyl cellulose in order finally to obtain the finished coated tablets at an average weight of 406.7 mg of unit weight and each containing 100 mg of (−)-tartrate of the product of the invention.

EXPERIMENTAL PART

Preparation processes

*Example 1 (preferred)

a)

(+)-1-[(3,4,5-trimethoxy)benzyloxymethyl]-1-phenyl-N,N-dimethyl-n-propylamine

Into a reactor, protected from humidity and under nitrogen atmosphere, are introduced 60 ml of anhydrous dioxan, then 6.20 g of sodium hydride in an 80% by weight suspension (w/w) in paraffin (0.207 mol).

While stirring and without exceeding 50° C., 40 g (0.207 mol) of (+)-2-dimethylamino-2-phenyl-butanol ($[\alpha]_D = +7.9°$; C=1, ethanol) are introduced. The suspension is stirred at 40° C. for a further 45 minutes, then cooled down to a temperature near 20° C.

Within 2 hours and without exceeding 50° C., 44.9 g (0.207 mol) of 3,4,5-trimethoxybenzyl chloride in 5 ml of anhydrous dioxan are introduced. The reaction medium is heated to 70°–75° C. and kept up at this temperature for 5 hours. After cooling down, the mixture is left overnight, then 200 ml of water are added slowly, while maintaining a temperature below 20° C. After acidification to pH 1 by sulphuric acid, it is extracted with 60 ml of toluene.

The toluene phase is isolated and removed. The acid phase is alkalized with a concentrated sodium hydroxide solution, then extracted twice with 150 ml of methylene chloride.

The combined organic phases are washed in water, then dried with $Na_2SO_4$. The solvent is distilled. The product obtained is in the form of a pale yellow, viscous oil.

Weight: 70.30 g.
Yield: 91%.

1H - NMR - $CDCl_3$ (60 MHz, TMS int) - chemical shifts in ppm: 0.70 (triplet, 3H), 1.95 (quadruplet, 2H); 2.32 (singlet, 6H) 3.90 (singlet, 11H), 4.55 (singlet, 2H); 6.65 (singlet, 2H) 7.35 (broad, 5H).

$[\alpha]_D = +16.5°$(c=6, ethanol).

b) Salification by D-(−)-tartaric acid 3.50 g (9.38 mmol) of the dextrorotatory enantiomer prepared as above, 1.37 g (9.13 mmol) of D-(−)-tartaric acid and 21 ml of absolute ethanol are introduced into a reactor.

While stirring, the mixture is heated to 50° C. and kept at this temperature for 30 minutes. The solution is gradually cooled down to approximately 10° C. within 16 hours. The crystals are filtered and dried in vacuo at 50° C. until they reach a constant weight.

Weight: 4.06 g.
Yield = 85%.
mp = 147° C.
$[\alpha]_D^{25} = +14.5°$ (c=5, HCl N).

A sample of this product is recrystallised in boiling ethanol (5 volumes per part by weight). The crystals obtained have a melting point and an optical rotation which are identical to the product before treatment. In conclusion, the values of the melting point and the optical rotation mentioned above are considered to be characteristic of the purified product.

*Example 2 a) Resolution of the racemic compound

Into a reactor, protected from humidity, 210 ml of absolute ethanol, 30 g (80.3 mmol) of (+/−)-1-[(3,4,5-trimethoxy)benzyloxymethyl]-1-phenyl-N,N-dimethyl-n-propylamine are introduced. Then 9.6 g (64.2 mmol) of L-(+)-tartaric acid are added and, while stirring, the mixture is heated under reflux which is kept up for 15 minutes.

The solution obtained is gradually cooled down to 20° C., while stirring, then left for one night.

The undissolved part is filtered and removed. It contains essentially the L-(+)-tartrate of the levorotatory enantiomer of the product of the invention which is purified in order to obtain a sample for comparison, by recrystallizing it in absolute ethanol at the rate of 5 volumes per parts by weight of product until it reaches a constant optical rotation:

$[\alpha]_D = -14.5°$ (c=5, HCl N).

The alcoholic filtrate of the first crystallisation containing the product of the invention is evaporated in vacuo and the residue dissolved in 160 ml of water.

The solution is alkalized to pH 10 with a concentrated sodium hydroxide solution, then extracted twice with 120 ml of methylene chloride. The combined organic phases are washed in water, then dried with $Na_2SO_4$. After removal of the methylene chloride by distillation, a pale yellow, oily residue enriched in dextrorotatory isomer is obtained.

Weight: 16.50 g.
Yield by weight: 55%.
$[\alpha] = +14.7°$ (c=6, ethanol) - optical purity = 89%.

b) Salification by D-(−)-tartaric acid

The method described in b) of Example 1 is then followed, using 12.6 g (33.7 mmol) of the former product and 5.05 g (33.7 mmol) of D-(−)-tartaric acid in 110 ml of anhydrous ethanol. The crystallized product is filtered and dried.

Weight: 13.8 g.
Yield by weight: 78%.
mp=143°–145° C. $[\alpha]_D^{25}=+13.8°$ (c=5, HCl N).
optical purity=95%.

The product is recrystallized in 65 ml of ethanol under reflux. After having been cooled down slowly to 20° C., while stirring, the crystals are filtered and dried in vacuo until they reach a constant weight.

Weight: 12.4 g.
Yield by weight: 90%.
mp=147° C. $[\alpha]_D^{25}=+13.8°$ (c=5, HCl N).

A sample product is treated in an alkali medium and extracted with methylene chloride. The pale yellow, oily residue obtained after evaporation has an optical rotation $[\alpha]_D$ of +16.6° at a concentration of 6% (w/v) in ethanol. When calculated, this value is considered to be characteristic of the optical purity of the dextrorotatory isomer which is the object of the invention.

We claim:

1. A method of stimulating gastric emptying in an animal in the essential absence of any analgesic effect which comprises administering to an animal an effective dosage of crystallized (+)-1-[(3,4,5-trimethoxy)-benzyloxymethyl]-1-phenyl-N,N-dimethyl-N-propylamine having the formula

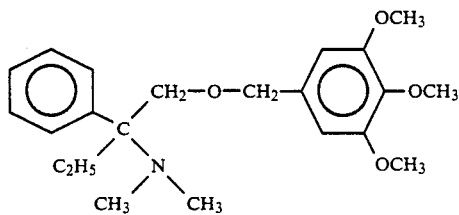

or its pharmaceutically acceptable acid addition salt.

2. The method of claim 1 wherein the salt is (+)-1-[(3,4,5-trimethoxy)-benzyloxymethyl]-1-phenyl-N,N-dimethyl-N-propylamine D-(−)-tartrate.

3. A process for normalizing the gastrointestinal tract of a patient treated with an analgesic compound comprising administering to said patient in an amount effective to normalize the gastrointestinal tract crystallized (+)-1-[(3,4,5-trimethoxy)-benzyloxymethyl]-1-phenyl-N,N-dimethyl-N-propylamine having the formula

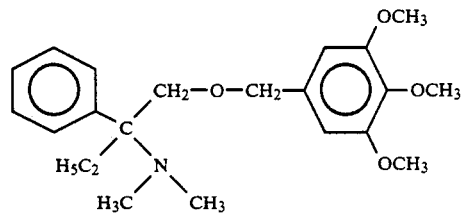

or its pharmaceutically acceptable acid addition salt.

4. A method for increasing gastric discharge in a subject which comprises administering to the subject a medicament consisting essentially of the (+) enantiomer of 1-[(3,4,5-trimethoxy)-benzyloxymethyl]-1-phenyl-N,N-dimethyl-n-propylamine or a pharmaceutically acceptable acid addition salt thereof in a crystallized form and in an amount which is therapeutically effective to increase the gastric discharge of solids from the subject and to provide antispasmodic activity while substantially avoiding the generation of analgesic activity.

5. The method of claim 4 which further comprises forming the acid addition salt by reaction with an optically active enantiomer of an organic acid.

6. The method of claim 4 which further comprises forming the acid addition salt by reaction with D(−)tartaric acid.

7. The method of claim 4 which further comprises preparing the (+) enantiomer by forming a metallic alcoholate of (+)-2-dimethylamino-2-phenyl-n-butanol and condensing the alcoholate with a 3,4,5-trimethoxy benzyl halide.

8. The method of claim 4 which further comprises preparing the (+) enantiomer by forming diastereomers of racemic 1-[(3,4,5-trimethoxy-benzyloxymethyl]-1-phenyl-N,N-dimethyl-n-propylamine with a (+) enantiomer of an organic acid, removing the (−) enantiomer of the amine by crystallization and separation from the remaining filtrate and treating the filtrate to obtain the (+) enantiomer of the amine.

9. The method of claim 4 which further comprises preparing the (+) enantiomer by forming diastereomers of racemic 1-(3,4,5-trimethoxy)-benzyloxymethyl]-1-phenyl-N,N-dimethyl-n-propylamine with a L-(+)-tartaric acid, removing the (−) enantiomer of the amine by crystallization and subsequent separation from the remaining filtrate and treating the filtrate to obtain the (+) enantiomer of the amine.

10. The method of one of claims 7, 8 or 9 which further comprises forming the acid addition salt by reaction with D(−)tartaric acid to purify the (+) enantiomer salt of the amine.

11. The method of claim 4 which further comprises administering the medicament at a daily therapeutic dose of between about 5 and 1000 mg of the (+) enantiomer.

12. The method of claim 4 which further comprises preparing the medicament in the form of a tablet, capsule, suppository, solution or suspension.

13. The method of claim 12 wherein the (+) enantiomer constitutes at least about 5 to 80% by weight of the medicament.

14. The method of claim 12 wherein the medicament is in the form of an aqueous solution or suspension with the (+) enantiomer constitutes at least about 0.1 to 20% by weight thereof.

15. The method of claim 4 wherein the gastric discharge is increased by at least about 4 times as much as the corresponding (−) enantiomer of the amine and wherein the D50 toxicity of the (+) enantiomer is less than one-half that of the corresponding (−) enantiomer of the amine.

16. A method for normalizing the activity of the gastrointestinal tract of a subject who has been treated with analgesic compounds, which comprises administering to the subject a medicament consisting essentially of the (+) enantiomer of 1-[(3,4,5-trimethoxy)-benzyloxymethyl]-1-phenyl-N,N-dimethyl-n-propylamine or a pharmaceutically acceptable acid addition salt thereof in a crystallized form and in an amount which is therapeutically effective to increase the gastric discharge of solids from the subject and to provide antispasmodic activity so that the effects of the analgesic compounds are reduced and the gastrointestinal tract activity is substantially returned to normal.

17. The method of claim 16 which further comprises forming the acid addition salt by reaction with an optically active enantiomer of an organic acid.

18. The method of claim 16 which further comprises forming the acid addition salt by reaction with D(−)tartaric acid.

19. The method of claim 16 which further comprises preparing the (+) enantiomer by forming a metallic alcoholate of (+)-2-dimethylamine-2-phenyl-n-butanol and condensing the alcoholate with a 3,4,5-trimethoxy benzyl halide.

20. The method of claim 16 which further comprises preparing the (+) enantiomer by forming diastereomers of racemic 1-[(3,4,5-trimethoxy)-benzyloxymethyl]-1-phenyl-N,N-dimethyl-n-propylamine with a (+) enantiomer of an organic acid, removing the (−) enantiomer of the amine by crystallization and separation from the remaining filtrate and treating the filtrate to obtain the (+) enantiomer of the amine.

21. The method of claim 16 which further comprises preparing the (+) enantiomer by forming diastereomers of racemic 1-[(3,4,5-trimethoxy)-benzyloxymethyl]-1-phenyl-N,N-dimethyl-n-propylamine with a L-(+)-tartaric acid, removing the (−) enantiomer of the amine by crystallization and subsequent separation from the remaining filtrate and treating the filtrate to obtain the (+) enantiomer of the amine.

22. The method of one of claims 19, 20 or 21 which further comprises forming the acid addition salt by reaction with D(−)tartaric acid to purify the (+) enantiomer salt of the amine.

23. The method of claim 16 which further comprises administering the medicament at a daily therapeutic dose of between about 5 and 1000 mg of the (+) enantiomer.

24. The method of claim 23 which further comprises preparing the medicament in the form of a tablet, capsule, suppository, solution or suspension.

25. The method of claim 24 wherein the (+) enantiomer constitutes at least about 5 to 80% by weight of the medicament.

26. The method of claim 24 wherein the medicament is in the form of an aqueous solution or suspension with the (+) enantiomer constitutes at least about 0.1 to 20% by weight thereof.

27. The method of claim 16 wherein the gastric discharge is increased by at least about 4 times as much as the corresponding (−) enantiomer of the amine and wherein the $D_{50}$ toxicity of the (+) enantiomer is less than one-half that of the corresponding (−) enantiomer of the amine.

* * * * *